United States Patent [19]

Nahum

[11] Patent Number: 4,545,087

[45] Date of Patent: Oct. 8, 1985

[54] TOOTHBRUSH

[76] Inventor: Sylvain Nahum, 16 Ave. Dumas, CH-1206 Geneva, Switzerland

[21] Appl. No.: 527,739

[22] Filed: Aug. 30, 1983

[30] Foreign Application Priority Data

Dec. 30, 1981 [CH] Switzerland ............... 8345/81

[51] Int. Cl.⁴ .................................. A46B 13/02
[52] U.S. Cl. .......................................... 15/22 R
[58] Field of Search ............... 15/22 R, 22 A, 22 C, 15/167 R; 128/62 A

[56] References Cited

U.S. PATENT DOCUMENTS 4,156,620  5/1979  Clemens ................ 15/22 R

FOREIGN PATENT DOCUMENTS 1112966  8/1961  Fed. Rep. of Germany ..... 15/22 R

*Primary Examiner*—Edward L. Roberts

*Attorney, Agent, or Firm*—Robert E. Burns; Emmanuel J. Lobato; Bruce L. Adams

[57] ABSTRACT

A toothbrush has a handle and a head portion in which tufts of bristles are mounted in two different types of supports. Supports of a first type are mounted in the head portion for oscillation about axes perpendicular to the length of the bristles so as to be oscillated by rectilinear motion of the toothbrush on the teeth. At least one rack is connected with inner ends of supports of the first type so as to be reciprocated by oscillation of the supports. Supports of a second type are mounted in the head portion for rotation about axes parallel to the length of the bristles. Pinions on the inner ends of supports of the second type mesh with the rack or racks connected with supports of the first type so that the pinions and respective supports of the second type are rotated upon reciprocation of the rack of racks by oscillation by supports of the first type.

12 Claims, 10 Drawing Figures

TOOTHBRUSH

The present invention relates to a tooth brush made up of a handle and of a head in which bristle tufts are mounted on movable supports automatically put into motion when the user, after having applied the bristles against his teeth, gives the brush he holds by the handle a reciprocating rectilinear movement in the vertical or horizontal direction.

In known tooth brushes of this type, the movable supports all carry out the same movement, for instance a rotary movement or an oscillating movement, so that the bristles do not properly sweep the surface of the teeth and thus do not provide an adequate cleaning thereof.

It is an object of the present invention to improve the quality and the efficiency of tooth cleaning.

The tooth brush of the present invention is characterized by the fact that it comprises at least one movable support of a first type so adapted that the bristle tuft or tufts which it carries are capable of oscillatng in planes that are perpendicular to the plane of the brush; movable supports of a second type adapted so that the bristle tufts that they carry are capable of rotating about their respective axes of symmetry, and a mechanism kinetically connecting the said movable supports together in such a manner that during cleaning the oscillating bristle tufts rock alternately in one direction or the other while driving the rotary bristle tufts into reciprocating rotation.

Two preferred embodiments of the invention will now be described having reference to the appended drawing wherein.

Figure 7:
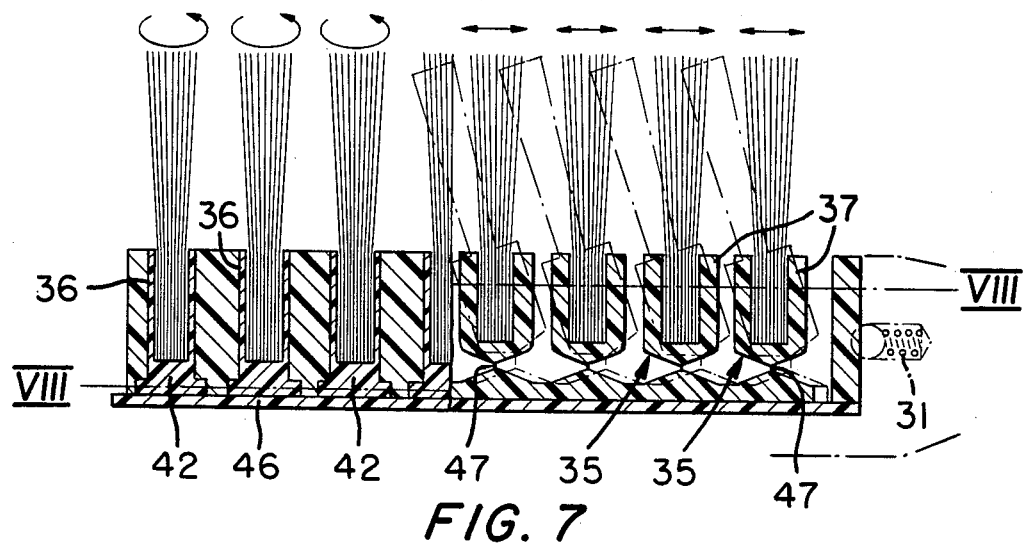
Figure 8:
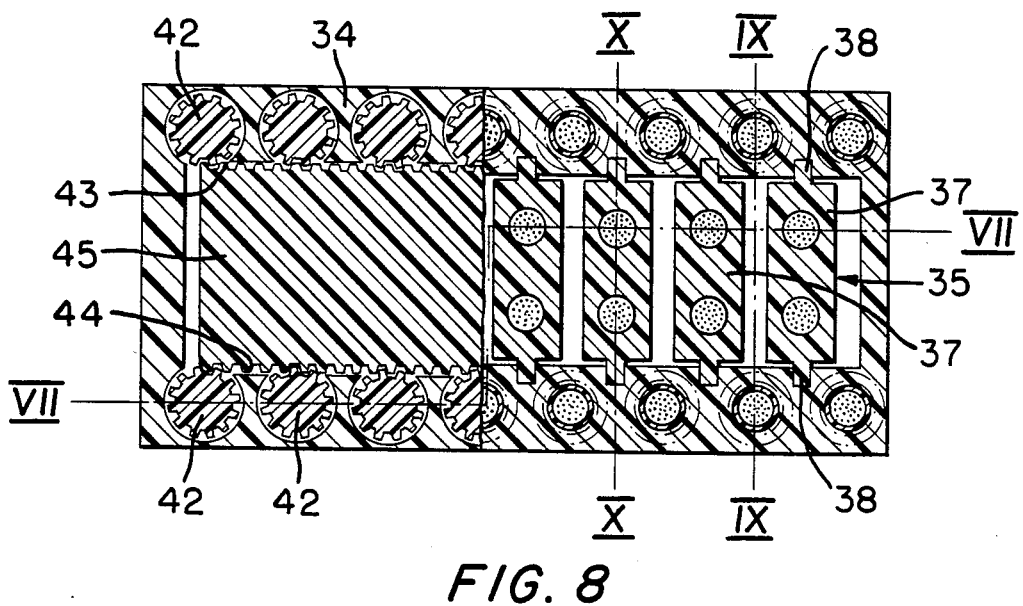
Figures 9, 10:
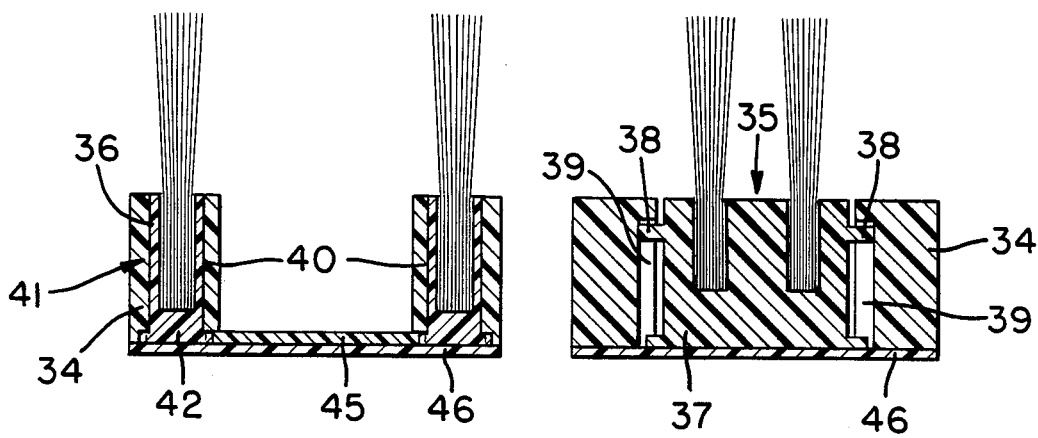

FIGS. 7 and 8 are cross-sectional views of the head of the tooth brush along lines VII—VII and VIII—VIII of FIGS. 8 and 7 respectively, and FIGS. 9 and 10 are cross-sectional views along lines IX—IX and X—X of FIG. 8.

The tooth brush illustrated in FIGS. 1 to 4 is constituted by a head portion 10 formed of a body 11 extending into a handle 12 and of a cover 13 clipped over the body 11 by a pressure device 14.

The bristle tufts are carried by movable supports of two types mounted in the cover 13; rocking supports 15 and rotary supports 16 arranged respectively in three and five transverse rows.

Figure 1:
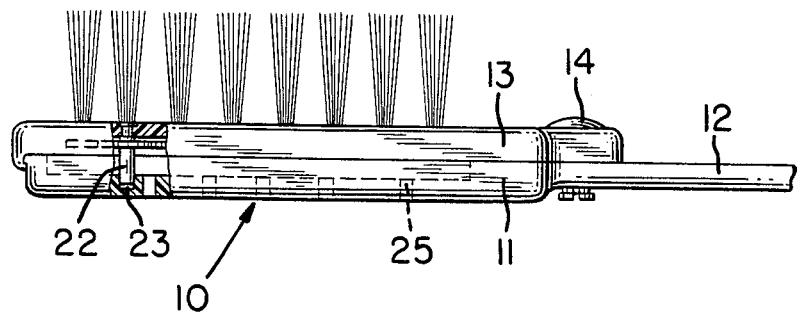
FIG. 1 is a side elevation view of a first embodiment, partly broken away.
Figure 2:
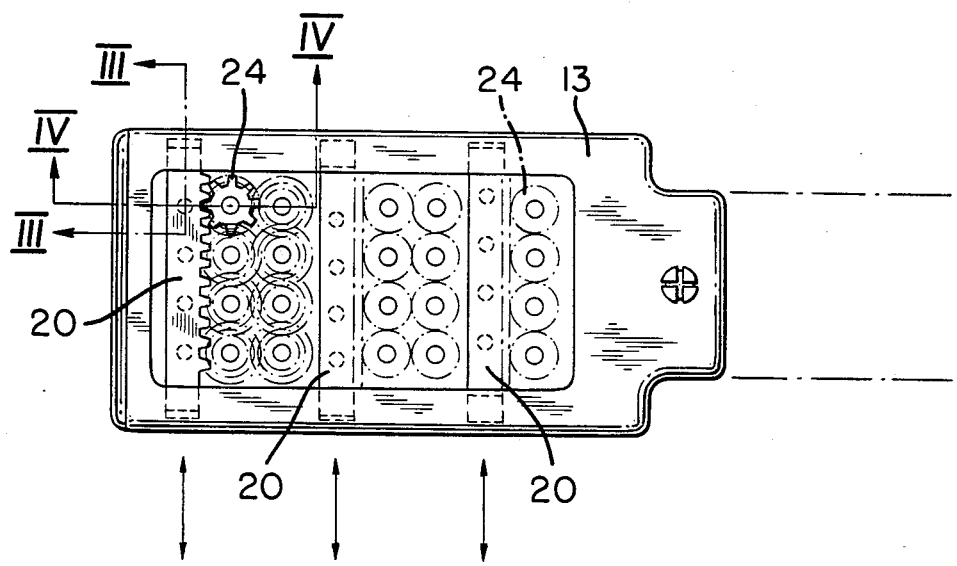
FIG. 2 is a plan view of the brush of FIG. 1.
Figure 3:
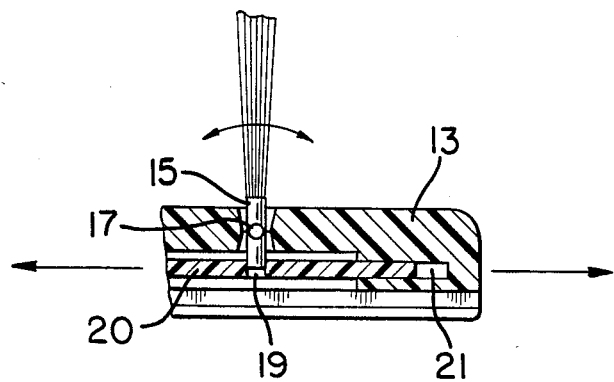
FIGS. 3 and 4 are cross-sectional views of parts of the tooth brush of this embodiment, taken along line III—III and IV—IV of FIG. 2.
Figure 4:
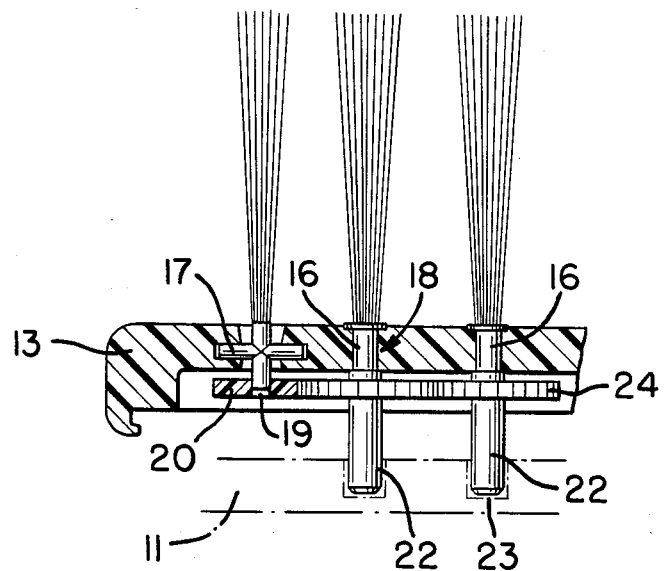
Figure 5:
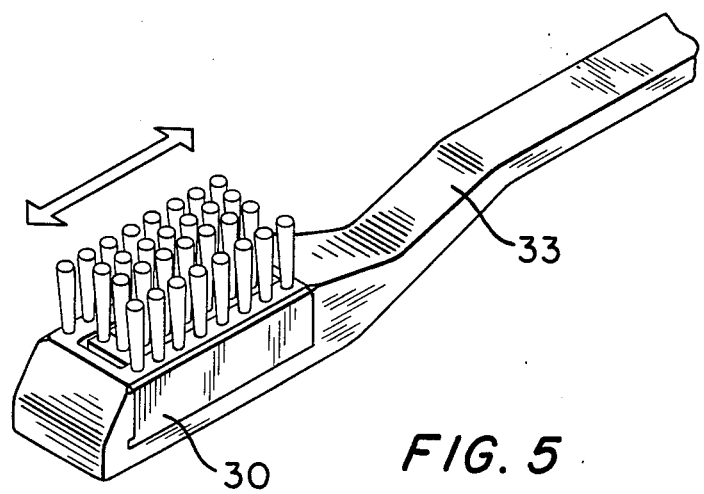
FIG. 5 is a perspective view of a tooth brush according to a second embodiment.
Figure 6:
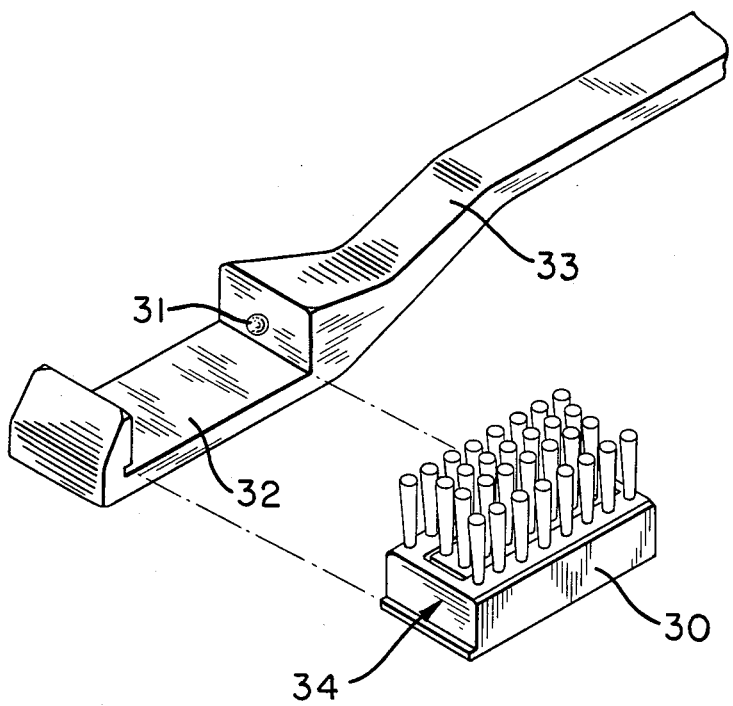
FIG. 6 is a view similar to that of FIG. 5 but in exploded form.

The supports 15 pivot on axles 17 and have lower extensions that engage into apertures 19 of a rack 20 slideable in a guide 21, see FIG. 3.

The supports 16 rotate in bearings 18. Each extends downwardly into a pivot extension 22 received in a socket 23 in the body 11 and on which is keyed a pinion 24 received in a housing 23 defined in the lower surface of the cover 13.

The pinions 24 of the first row of supports 16 simultaneously mesh with the rack 20 of the first row of supports 15 and with the pinions 24 of the second row of supports 16. The pinions 24 of the third row of supports 16 are simultaneously in mesh with the rack of the second row of supports 15 and with the pinions 24 of the fourth row of supports 16. Finally, the rack 20 of the third row of supports 15 is in mesh with the pinions 24 of the fifth row of supports 16.

When the user applies the bristles on his teeth and drives the tooth brush into a vertical reciprocating rectilinear movement, the bristle tufts mounted on the rocking supports 15 oscillate while giving the racks 20 a corresponding movement during which the rotary supports 16 are driven into alternative rotation.

During these various movements, the tufts mounted on the rocking supports 15 linearly sweep the surface of the teeth while the tufts mounted on the rotary supports 15 penetrate into the teeth interspaces.

The conjugation of these various movements results in a particularly efficient cleaning of the teeth.

To wash the tooth brush after use, it is sufficient to unclip the cover 13 and wash it under water as well as the body 11. It will be noted that holes 25 are provided through the base to facilitate drainage of of tooth paste that may have filtered into the bottom of the case.

Advantageously, the above tooth brush is made of plastics material, either molded or injected, including the racks 20 and the pinions 24.

The tooth brush shown in FIGS. 5 to 10 is made up of cassette 30 removably secured, by means of a ball lock 31, in an ad-hoc housing 32 of the handle 33.

This cassette 30, entirely made of plastics material, is formed of a case 34 comprising four longitudinal rows of bristles tufts mounted on movable supports of two types, rocking supports 35 and rotary supports 36.

The rocking or oscillating supports 35 each carries two bristle tufts and form the two central rows. They are constituted by blocks 37 provided laterally with pins 38 engaging into vertical grooves 39 provided in the lateral faces of the longitudinal walls of the case 34. The bristle tufts mounted on these supports 35 may thus oscillate as illustrated in the drawing in planes that are perpendicular to the plane of the tooth brush.

The rotary supports 36 are constituted by sleeves 40, each having a bristle tuft, rotatably mounted in corresponding cylindrical holes 41 provided vertically in the longitudinal walls of the case 34. The bristle tufts mounted on these supports 36 may thus rotate as illustrated in the drawings, about their respective symmetry axes.

The sleeves 40 are terminated at the bottom by pinions 42 which mesh with the teeth 43 and 44 of a rack 45 bearing, along with the pinions 42, on a base 46 which constitutes the bottom of the case 34.

The seven blocks 37 are molded integrally with the rack 45 and each has, in their lower zone, a thin portion 47 which acts as an articulation (see FIG. 7).

When the user applies the bristles on his teeth and drives the tooth brush, he holds by the handle, into a horizontal reciprocating movement, the bristle tufts mounted on the rocking supports 35 oscillate while communicating a corresponding movement to the rack 45 during which the rotary supports 36 are driven into alternative rotation.

As in the first embodiment described above, the conjugated actions of the rocking bristles and of the rotary bristles ensure a particularly efficient brushing of the teeth.

A particularly important feature of this second embodiment resides in the fact that the head of the tooth brush is in the form of a cassette that may be replaced by a new cassette when the bristles are worn out or by a cassette of which the bristles have different features, for instance the bristles are harder or the bristles of the rocking tufts are different from those of the rotary tufts.

Mas produced, this tooth brush could be made at a price so low that it will be possible to sell cassettes adapted to be discarded after they have been used a certain number of times.

Under these conditions, it is possible to imagine the manufacture of tooth brushes with discardable cassettes having a particularly well made handle from as esthetic point of view, for instance made of a precious metal, engraved, embossed or patterned, even personalized with initials, interlacing or other signs.

According to a variant, there could be only one single rocking support carrying one or several bristle tufts.

I claim:

1. A tooth brush comprising a handle and a head portion in which are mounted movable supports in which tufts of bristles are secured and from which said bristles project, said supports comprising at least one support of a first type mounted in said head portion for oscillation about an axis generally perpendicular to the bristles upon movement of said head portion rectilinearly in the plane of oscillation of said tufts, and a plurality of supports of a second type each mounted in said head portion for rotation individually about an axis generally parallel to the bristles, and means mechanically interconnecting said supports of said first type and said second type so that oscillation of said support of the first type causes rotation of said supports of the second type about their respective axes.

2. A tooth brush as claimed in claim 1, in which said plane of oscillation of said tufts of bristles of said support of the first type lies parallel to the longitudinal axis of said handle.

3. A tooth brush as claimed in claim 1, in which said plane of oscillation of said tufts of bristles of said support of the first type lies transverse to the longitudinal axis of said handle.

4. A tooth brush as claimed in claim 1, in which said mechanically interconnecting means include at least one rack connected with said support of the first type and pinions connected with said supports of the second type.

5. A tooth brush as claimed in claim 4, in which a plurality of supports of the first type are aligned in at least one row and a plurality of supports of the second type are aligned in at least one row, said rows being parallel; each of said supports having a lower extension, said rack being connected to the ends of said lower extensions of said supports of the first type, whereby oscillation of said supports of said first type causes reciprocating rectilinear motion of said rack and, each pinion being mounted on one of said lower extensions of said supports of said second type; said pinions of said supports of said second type meshing with said rack whereby rectilinear reciprocation of said rack causes rotary oscillation of said pinions on said lower extensions of supports of the second type.

6. A tooth brush comprising a handle and a head portion in which are mounted rows of movable supports in which tufts of bristles are secured and from which said bristles project, said supports comprising a plurality of supports in at least one row which are of a first type mounted in said head portion for oscillation about axes generally perpendicular to the bristles upon movement of said head portion rectilinearly in the plane of oscillation of said supports and tufts, and a plurality of supports in at least one other row which are of a second type mounted in said head for rotation about respective axes generally parallel to the bristles, and means mechanically interconnecting said supports of said first type with said supports of said second type, so that oscillation of said supports of said first type causes rotation of sais supports for said second type about their respective axes.

7. A tooth brush according to claim 6, in which said mechanical interconnecting means comprises at least one rack connected with inner ends of said supports of said first type and reciprocated by oscillation of said supports of said first type, and pinions connected respectively with inner ends of said supports of said second type and meshing with said rack for rotation of said pinions by reciprocation of said rack.

8. A tooth brush according to claim 6, in which there are a plurality of spaced rows of said supports of said first type extending transversely to the longitudinal direction of said handle.

9. A tooth brush according to claim 6, in which said row of supports of said first type extends at least approximately parallel to the longitudinal direction of said handle along side of rows of supports of said second type.

10. A tooth brush according to claim 6, in which said head portion comprises two removably interconnected parts defining a case, said mechanical interconnecting means being located in said case and said bristles extending out of said case.

11. A tooth brush according to claim 10, in which said case comprises a base portion integral with said handle and a cover removably secured to said base portion.

12. A tooth brush according to claim 10, in which said case comprises a housing integral with said housing and a cassette removably received in said housing, said supports and mechanical connecting means being located in said cassette.

* * * * *